United States Patent [19]

Pearson et al.

[11] 4,407,800

[45] Oct. 4, 1983

[54] PROTOZOACIDAL ACTIVITY OF PHENOTHIAZINES

[75] Inventors: Richard D. Pearson, Charlottesville; Erik L. Hewlett, Keswick, both of Va.

[73] Assignee: University of Virginia Alumni Patents Foundation, Charlottesville, Va.

[21] Appl. No.: 317,547

[22] Filed: Nov. 2, 1981

[51] Int. Cl.³ .............................................. A61K 31/54
[52] U.S. Cl. ................................................. 424/247
[58] Field of Search ........................... 424/247; 544/35

[56] References Cited

PUBLICATIONS

*Current Therapy,* H. F. Conn, W. B. Saunders Co., Phila., Lond., Tor., 1981, pp. 39–40.

The Pharmacological Basis of Theraputics, Goodman et al., MacMil., 1980, pp. 417–418.
Chem. Abstr., vol. 87, 1977, p. 585, Ab. No. 152101t, Savelli et al., Derivatives of 2-phenothiazine . . . .
Merck Index, 9th ed., Merck Co., p. 850, No. 6363.
*Medical Parasitology in the Tropics,* Nnochiri, E., Oxford Press, Lond., 1975, p. 123.

*Primary Examiner*—Jerome D. Goldberg
*Assistant Examiner*—John W. Rollins, Jr.
*Attorney, Agent, or Firm*—Oblon, Fisher, Spivak, McClelland & Maier

[57] ABSTRACT

A method of treating or protecting against parasitic diseases caused by members of the protozoan family Trypanosomatidae comprising administering to a mammal a phenothiazine drug. This represents a new use of the phenothiazine compounds.

11 Claims, 3 Drawing Figures

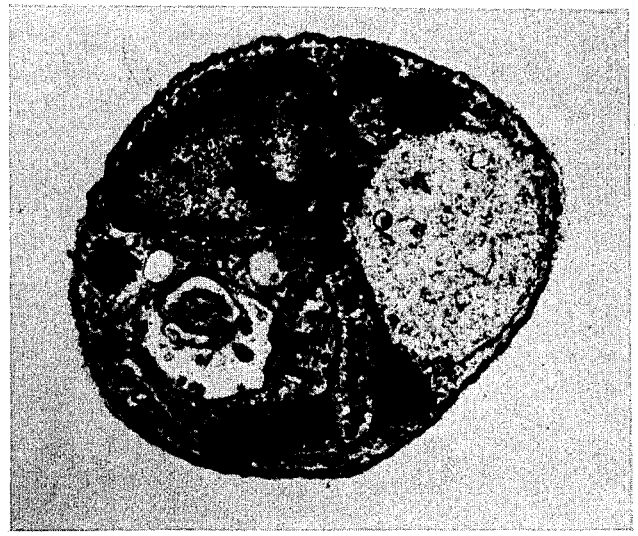
FIG. 1A  x 14k
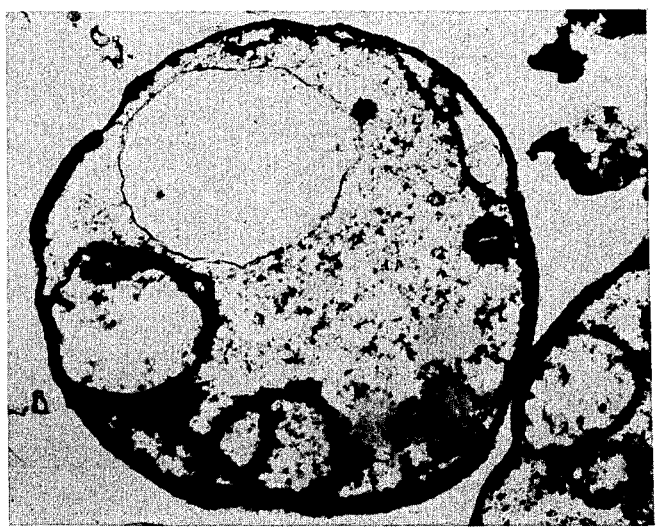
FIG. 1B  x 14k

PROTOZOACIDAL ACTIVITY OF PHENOTHIAZINES

BACKGROUND OF THE INVENTION

1. Field of the Invention

This invention relates to a new use of the phenothiazine drugs and more particularly to their use as protozoacides against members of the protozoan family Trypanosomatidae.

2. Description of the Prior Art

The Trypanosoma and Leishmania are the only genera of the family Trypanosomatidae that are pathogenic for humans or animals. The first genus, Trypanosoma, causes a group of closely related disease of man and animals known as trypanosomiasis. Two general forms of the disease are recognized: African trypanosomiasis, occurring mainly but not exclusively in tropical Africa, and American trypanosomiasis or Chagas' disease, which occurs mainly in Central and South America. Various forms of the disease caused by different species of protozoa include sleeping sickness (humans and cattle), nagana (domestic animals), secadera (domestic animals), surra disease (domestic animals), mal de caderas (horses), and Chagas' disease (humans). The second pathogenic genus, Leishmania, consists of intracellular parasites that cause a complex of diseases known as leishmaniasis. Two forms of the disease are recognized: visceral leishmaniasis caused by L. donovani and known as kala-azar (black fever), and mucocutaneous and cutaneous leishmaniasis, caused by L. tropica, L. mexicana, and L. braziliensis and known by various names, including oriental sore, espundia, and Bay sore. Leishmania change in form when transmitted from insects to mammals. The amastigote stage is found within white cells in the mammalian host. The promastigote stage of the organism is found only in the insect host. When a sandfly bites a susceptible host, promastigotes are inoculated, convert to amastigotes, and go on to produce disease. When the sandfly bites a mammal with leishmaniasis, it acquires amastigotes which convert to promastigotes in its gut.

There is now no uniformly effective, non-toxic form of therapy for any of the major tropical diseases of humans or domestic animals caused by these parasites. Chemotherapy has been tried but with only limited success. Suramin,

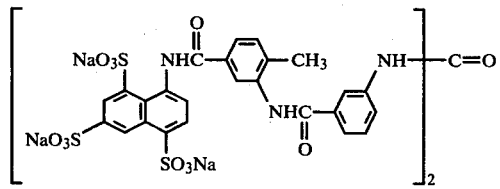

is active against some trypanosome infections but is not active against T. cruzi. In addition, an unacceptable incidence of local severe reactions in patients after intramuscular injection precludes wide spread usage for humans. Arsenicals and antimonials have found use against both leishmaniasis and trypanosomiasis, but have obvious limitations because of their general toxicity. Nevertheless, tryparsamide is still widely used in the treatment of West African sleeping sickness and sodium stibogluconate has remained one of the drugs of choice available in the treatment of leishmaniasis.

Tryparsamide

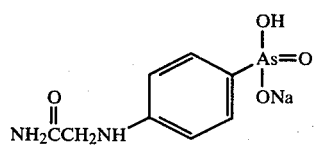

Sodium stibogluconate

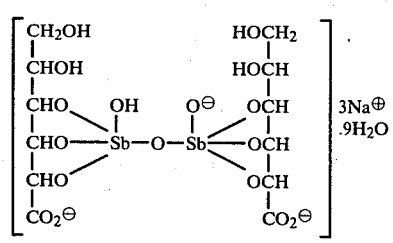

The chemotherapy of both trypanosomiasis and leishmaniasis is reviewed in W. J. Ross, "Chemotherapy of Trypanosomiasis and other Protozoan Diseases", *Burger's Medicinal Chemistry*, 4th Ed., Part II, pp. 439–479, M. E. Wolff, ed., John Wiley & Sons, New York (1979).

Because of the deleterious side effects of known chemotherapeutic agents, a continuing need for new protozoacides against Trypanosomatidae exists. In addition, because the diseases caused by these protozoa occur principally in the underdeveloped nations of the world, a drug that can be administered orally by unskilled workers and which has known, minimal side effects is highly desirable.

SUMMARY OF THE INVENTION

Accordingly, it is an object of this invention to provide a protozoacide effective against members of the family Typranosomatidae that does not suffer from disadvantageous toxic side effects.

It is a further object of this invention to provide a protozoacide effective against members of the family Typanosomatidae that may be admistered orally with minimal supervision.

It is a further object of this invention to provide a protozoacide effective against members of the family Typanosomatidae that is selected from a class of known drugs proven safe for human usage.

These and other objects of the invention as will hereinafter become more readily apparent have been accomplished by providing a method of treating trypanosomiasis and leishmaniasis comprising the step of administering to a mammal suspected of having trypanosomiasis or leishmaniasis an amount effective to reduce the number of living protozoa in said mammal of a phenothiazine compound having a formula selected from the group consisting of

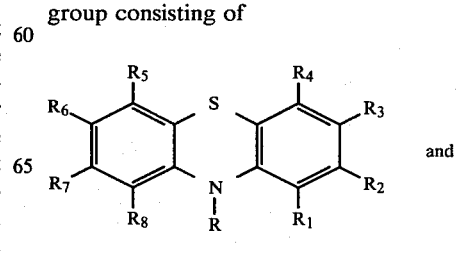

and

-continued

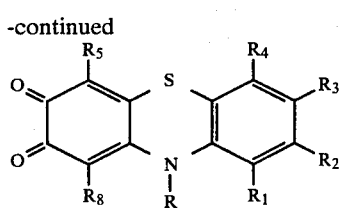

wherein R=hydrogen or $C_1$–$C_5$ alkyl, wherein said alkyl may be substituted by an organic functional group containing oxygen, nitrogen, sulfur, phosphorus, or halogen, or by a phenyl, 5- or 6-membered cycloalkyl, or 5- or 6-membered heterocyclic ring containing nitrogen, oxygen, or sulfur, and $R_1$–$R_8$ independently represent hydrogen, a halogen atom, an organic functional group containing oxygen, nitrogen, sulfur, or phosphorous, or a $C_1$–$C_5$ alkyl $C_1$–$C_6$ acyl, phenyl, 5- or 6-membered cycloalkyl, or 5- or 6-membered heterocyclic radical containing nitrogen, oxygen, or sulfur, with the proviso that any two of $R_1$–$R_8$ may independently represent a 5- or 6-membered aliphatic, aromatic, or heterocyclic ring when taken together with the ring atoms of said phenothiazone compound.

BRIEF DESCRIPTION OF THE DRAWINGS

A more complete appreciation of the invention and many of the attendant advantages thereof will be readily obtained as the same become better understood by reference to the following detailed description when considered in connection with the accompanying drawings, wherein:

FIG. 1 shows electron micrographs of normal promastigotes of *L. donovani* (A) and promastigotes exposed to chlorpromazine (B);

DESCRIPTION OF THE PREFERRED EMBODIMENTS

Figure 2:
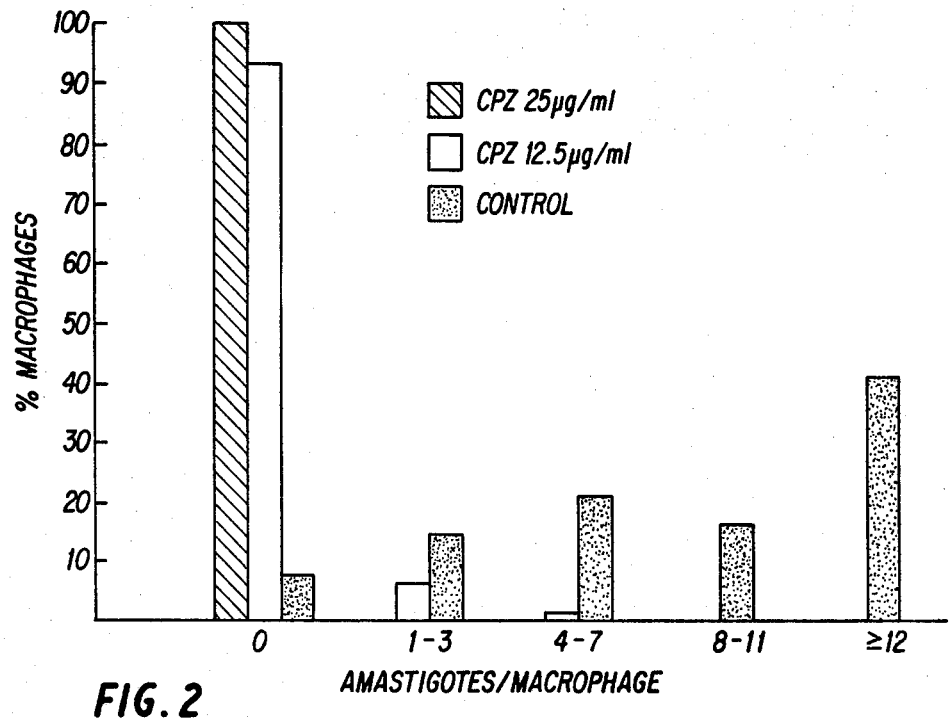
FIG. 2 shows the effect of chlorpromazine on amastigotes in human monocyte-derived macrophages by plotting the percentage of macrophages as a function of the degree of infection.

The present inventors have discovered that drugs of the phenothiazine class can kill members of the protozoan family Trypanosomatidae and thus have potential for use in the treatment of leishmaniasis, American trypanosomiasis, and African trypanosomiasis. The phenothiazines are derivatives of the parent compound, phenothiazine, which has the following formula:

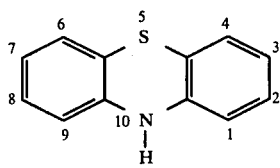

The phenothiazines as a class are widely used in medicine for the treatment of neuropsychiatric disorders and for the treatment of nausea and vomiting. However, prior to the present invention, they were not known to have protozoacidal activity against the Trypanosomatidae or against any other protozoan that is pathogenic for man. The use of the phenothiazines for treatment of infections caused by the Trypanosomatidae is a new and unpredicted use of this class of drugs.

All phenothiazines tested have shown protozoacidal activity, although, as is to be expected, the degree of activity has varied. Accordingly, it appears that any organic functional group may be substituted for one or more of the hydrogens of phenothiazine and at least some protozoacidal activity will remain. Suitable substituents for the aromatic rings include halogen; organic functional groups containing oxygen, such as hydroxyl, ester, and ether groups, nitrogen, such as amino, substituted amino, and amide groups, sulfur, such as thiol, thioether, and thioester groups, or phosphorous, such as phosphate groups; and substituents in which a carbon is attached directly to the aromatic ring, such as alkyl, acyl, aryl, cycloalkyl, and heterocyclic groups having no more than 6 carbons, including carbons or heteroatoms that alone or in combination form a 5- or 6-membered aliphatic, aromatic, or heterocyclic ring when taken together with the atoms of the aromatic rings of the phenothiazine. Suitable heterocyclic rings for all positions include pyridine, pyrrolidine, pyrrole, furan, tetrahydrofuran, and thiophene. Substituents at positions 2, 3, 7 and 8 are preferred. Most well-known and thoroughly studied phenothiazines have a single organic substituent at position 2, and such compounds, while not exclusively required, are preferred. Substituents that are electron-withdrawing with respect to hydrogen are preferred. Suitable electron-withdrawing substituents include halogen, trifluoromethyl, acyl, and sulfinyl. Of these the halogens, and especially chlorine, are most preferred.

Substitutions can also be made for the hydrogen on the nitrogen at position 10. Suitable substituents include alkyl and cycloalkyl groups having up to 20 carbons which may be substituted by any of the oxygen-, nitrogen-, sulfur-, phosphorus-, or halogen-containing functional groups, such as, for example, those discussed herein, or by one or more aryl, cycloalkyl, or heterocyclic ring having up to 10 carbons. Preferred are substituents in which a hetero atom, preferably nitrogen, is present at a position 3 or 4 atoms distant from the nitrogen of the phenothiazine ring. Suitable hetero atom-containing substituents include, among others, 3-(dimethylamino)propyl, 3-(4-methyl-1-piperazinyl)propyl, 2-(1-methyl-2-piperidyl)ethyl, (1-methyl-3-pyrrolidinyl)methyl, and their homologues.

Of the many different phenothiazines encompassed by this invention, it is especially preferred to use compounds that are currently approved for use in humans for other disorders, as the side effects and maximum dosages of these compounds are already known. The official, proprietary, and chemical names of some of these compounds are shown in Table 1.

TABLE 1

| Phenothiazine Derivatives | | |
|---|---|---|
| Official Name | Proprietary Name | Chemical Name |
| Chlorpromazine* | Thorazine | 2-chloro-10-[3-(dimethylamino)-propyl]phenothiazine |
| promazine+ | Sparine | 10-[3-(dimethylamino)propyl]-phenothiazine |
| triflupromazine+ | Vesprin | 2-trifluoromethyl-10-[3-(dimethylamino)propyl]phenothiazine |
| prochlorperazine* | Compazine | 2-chloro-10-[3-(4-methyl-1-piperazinyl)propyl]phenothiazine |
| trifluoperazine+ | Sterlazine | 2-trifluoromethyl-10-[3-(4-methyl-1-piperazinyl)propyl] |

TABLE 1-continued

Phenothiazine Derivatives

| Official Name | Proprietary Name | Chemical Name |
|---|---|---|
| | | phenothiazine |
| perphenazine+ | Trilafon | 2-chloro-10-(3-[4-(2-hydroxy-ethyl)-1-piperazinyl]propyl)-phenothiazine |
| fluphenazine* | Permitil Prolixin | 2-trifluoromethyl-10-(3-]4-(2-hydroxyethyl)-1-piperazinyl]-propyl)phenothiazine |
| acetophenazine+ | Tindal | 2-acetyl-10(3[4-(2-hydroxyethyl)-1-piperazinyl]propyl)phenothiazine |
| butaperazine | Repoise | 2-butyryl-10-[3-(4-methyl-1-piperazinyl)propyl]phenothiazine |
| carphenazine+ | Proketazine | 2-propionyl-10-(3-[4-(2-hydroxy-ethyl)-1-piperazinyl]propyl)-phenothiazine |
| thiopropazate | Dartal | 2-chloro-10-(3-[4-(2-hydroxy-ethyl)piperazinyl]propyl)-phenothiazine |
| piperacetazine+ | Quide | 2-acetyl-10-(3-[4-(2-hydroxy-ethyl)piperidino]propyl)-phenothiazine |
| thioridazine* | Mellaril | 2-methylthio-10-[2-(1-methyl-2-piperidyl)ethyl]phenothiazine |
| mesoridazine | Serentil | 2-methylsulfinyl-10-[2-(1-methyl-2-piperidyl)ethyl]phenothiazine |
| promethazine* | Phenergan | (±)-10-[2(2-dimethylamino)-propyl]phenothiazine |
| trimeprazine* | Temaril | (±)-10-[3-(dimethylamino)-2-methylpropyl]phenothiazine |
| methidilazine | Tacaryl | (±)-10-[(1-methyl-3-pyrrolidin-yl)methyl]phenothiazine |

*In USP XIX (1975).
+In NF XIV (1975).

Phenothiazines may be used to treat any mammal which is a host or potential host of a Trypanosomaditae protozoan. Humans and domestic animals, such as cattle, sheep, goats, pigs, horses, camels, or dogs, are the primary mammals for which protection is desired, although other mammals that are part of the life cycle of the parasites may also be treated.

Treatment consists of administering to a mammal suspected of being infected or which is exposed to danger of infection an amount of a phenothiazine effective in reducing the number of live parasites in the host mammal. It is preferred that a low initial dose be given with larger dosages being given later if the low dose does not prove effective. For adult humans, oral administration of 10 to 25 mg three times daily is a suitable starting dose. It is possible to give much higher dosages if needed. Up to 400 mg of chlorpromazine have been given four times daily to patients with severe psychiatric illness, and similar amounts are suitable for the present invention. For other mammals, equivalent dosages, based on a mg/kg basis, to those used with humans provide a suitable starting point from which changes can be made as necessary from species to species. A suitable starting dose would be about 0.2 to 0.5 mg/kg, with dosages up to 20 mg/kg being acceptable. Although oral administration is preferred, phenothiazines may be administered by intramuscular injection, which is particularly suitable for administration of high dosages (over 400 mg per day) to humans or for treatment of animals. Other methods of administration include intravenous injection and tubal feeding, either gastric or intestinal.

The phenothiazines may be administered in any non-toxic pharmaceutical carrier, including both solids and liquids, such as talc, sucrose, isotonic aqueous solutions, and water, in the form of a tablet, capsule, solution, or emulsion. It is also suitable to administer the phenothiazine together with a second drug known to be effective against leishmaniases or typanosomiasis in order to reduce the toxic effects of each drug while retaining high potency of the mixture. Suitable second drugs include suramin, tryparsamide, orsanine, pentamidine, diminazene, surfen C, prothidium, nifurtimox, sodium stibogluconate, and urea stibamine, as well as many others.

Pharmaceutical composition containing mixtures of phenothiazines and other protozoacides, such as those mentioned here and others having activity against Trypanosomatidae, may be prepared in advance and stored for easy use.

Having generally described the invention, a more complete understanding can be obtained by reference to certain specific examples, which are provided herein for purposes of illustration only and are not intended to be limiting unless otherwise specified.

EXAMPLE 1

A Sudanese strain of L. donovani was maintained by intracardiac inoculation of amastigotes into Syrian hamsters. At the time of study, spleens from animals infected 4-6 weeks previously were removed and homogenized in a tissue grinder. Amastigotes were isolated and used directly for study or allowed to convert to promastigotes in a modified growth medium (HO-MEM) at 26° C.

In the first study, promastigotes ($3\times10^6$/ml) were incubated with serial two-fold dilutions of various phenothiazines at 27° C. The concentration of motile or neutral-red-dye-stained promastigotes was determined at 18 hours. The minimal protozoacidal concentration (MPC) was defined as the lowest concentration that produced ≧90% reduction in viable promastigotes. Amastigotes were incubated with serial two-fold dilutions of phenothiazine at 37° C. in growth medium. The MPC was determined at 48 hours by counting the number of motile promastigotes.

As can be seen in Table 1, all five of the phenothiazine compounds tested had anti-leishmanial activity. Chlorpromazine and trifluoperazine were the most active against both promastigotes and extracellular amastigotes of *L. donovani.* Removal from chlorpromazine of the 2-chloro moiety (promazine), removal of the aliphatic side chain (2-chloro-phenothiazine), removal of both (phenothiazine) or oxidation of the ring sulfur (chlorpromazine sulfoxide) resulted in decreased activity as demonstrated in Table II. Changes in to the tricyclic ring or alteration of the aliphatic side chain results in several compounds which are active against Leishmania. In the case of the 7,8-dihydroxychlorpromazine and 7,8-dioxochlorpromazine, the activity against amastigotes was greater than chlorpromazine (Table II). Electron micrographs of normal promastigotes (FIG. 1*a*) and promastigotes exposed to chlorpromazine, 50 μg(micrograms)/ml for 25 minutes (FIG. 1*b*) indicate that chlorpromazine kills promastigotes. Exposure to the drug resulted in loss of nuclear and cytoplasmic detail and in some cases disruption of the plasma membrane.

TABLE I
ACTIVITY OF PHENOTHIAZINES AGAINST PROMASTIGOTES AND EXTRACELLULAR AMASTIGOTES OF L. DONOVANI

| DRUG | MEAN MPC ± SD (μg(micrograms)/ml) | |
|---|---|---|
| | PROMASTIGOTE | AMASTIGOTE |
| CHLORPROMAZINE | 14.6 ± 3.5 | 12.5 ± 0.0 |
| TRIFLUOPERAZINE | 15.6 ± 2.0 | 11.2 ± 1.2 |
| BUTAPERAZINE | 34.4 ± 4.7 | 12.5 |
| THIORIDAZINE | 25 | NS |
| PROMETHAZINE | 50 | NS |

NS = NOT STUDIED

TABLE II
VARIATIONS IN ACTIVITY OF PHENOTHIAZINES WITH STRUCTURE

| DRUG | MEAN MPC ± (μg(micrograms)/ml) | |
|---|---|---|
| | PROMASTIGOTE | AMASTIGOTE |
| CHLORPROMAZINE | 14.6 | 12.5 |
| PROMAZINE | 50 | 50 |
| 2-CHLOROPHENO-THIAZINE | >50 | >50 |
| PHENOTHIAZINE | >50 | >50 |
| CHLORPROMAZINE SULFOXIDE | >50 | >50 |
| 7,8-DIOXOCHLOR-PROMAZINE | 9.4 | 2.1 |
| 7,8-DIHYDROXY-CHLORPROMAZINE | 50 | 1.6 |
| 2-CHLORO-10-[3-AMINOPROPYL] PHENOTHIAZINE | 12.5 | N.S. |
| 7-HYDROXY-CHLORPROMAZINE | >50 | N.S. |
| 8-HYDROXY-CHLORPROMAZINE | >50 | N.S. |

N.S. = NOT STUDIED

EXAMPLE 2

Figure 3:
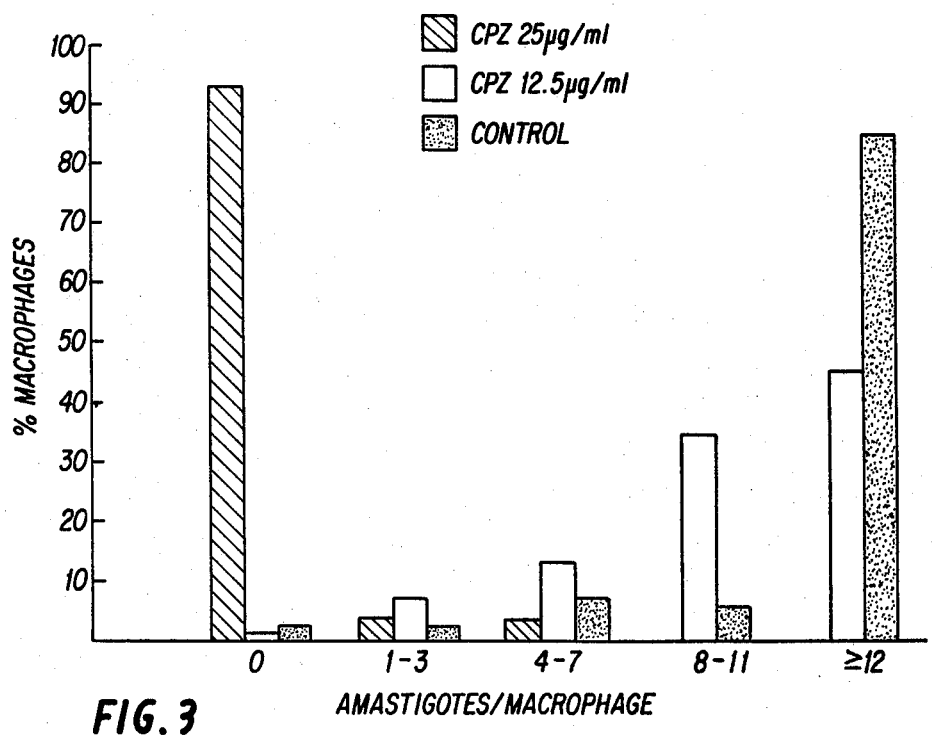
FIG. 3 shows the results of a second experiment identical to that shown in FIG. 2.

The effects of phenothiazines on amastigotes within human macrophages were also studied. Adherent human mononuclear cells were infected with amastigotes after 5 days of in vitro cultivation and exposed to serial two-fold dilutions of chlorpromazine, chlorpromazine sulfoxide, or no drug for 48 hours. The percentage of infected macrophages and the number of parasites per macrophage were determined by examining $\geq 200$ macrophages on Wright-Giemsa stained monolayers. The experiment demonstrated that chlorpromazine also kills amastigotes inside human monocyte-derived macrophages. The percentage of macrophages is plotted as a function of the degree of infection (number of parasites per macrophage) in two representative experiments, shown in FIGS. 2 and 3. Chlorpromazine, $\geq 12.5$ μg(micrograms)/ml, resulted in a shift to fewer parasites per macrophage. Chlorpromazine, less than 12.5 μg(micrograms)/ml, had no effect on the number of macrophages on the monolayer or on their morphology. Chlorpromazine sulfoxide, which was only weakly active against extracellular amastigotes or promastigotes, did not produce a measurable shift in the number of parasites per macrophage.

EXAMPLE 3

The anti-leishmanial effects of chlorpromazine were also demonstrated in vivo in an experimental model of visceral leishmaniasis. Weanling Syrian hamsters were infected with $1 \times 10^7$ amastigotes. On days 14–28, chlorpromazine (20 mg/kg) or saline were given through an oral cannula. On day 29, the hamsters were sacrificed and the number of amastigotes in the liver and spleen were determined. Livers were removed. Touch preparations were made and stained with a Wright-Giemsa preparation. The number of parasites per nucleus was determined. Spleens were also removed, homogenized, and cultured in promastigote growth medium at 27°. The number of promastigotes per spleen was determined after 48 hours. Chlorpromazine produced an 81% reduction in the number of amastigotes per nucleus in livers of Leishmania-infected hamsters (p<0.01) and a 72% reduction in the number of parasites isolated from infected spleens (p<0.01) as shown in Table III. Chlorpromazine treatment did not affect the behavior or weight of Leishmania-infected hamsters.

TABLE III
EFFECT OF CHLORPROMAZINE IN LEISHMANIA-INFECTED HAMSTERS

| | LIVER (AM/NUCLEUS) | SPLEEN (PM × 10⁷) |
|---|---|---|
| CONTROL | 3.28 ± 1.60 | 1.27 ± 0.28 |
| CHLORPROMAZINE TREATMENT | 0.63 ± 0.29* | 0.36 ± 0.22 |

*P $\leq$ 0.01 (STUDENT'S t-TEST)

The invention now being fully described, it will be apparent to one of ordinary skill in the art that many changes and modifications can be made thereto without departing from the spirit or scope of the invention as set forth herein.

What is claims as new and desired to be secured by Letters Patent of the United States is:

1. A method of treating trypanosomiasis and leishmaniasis comprising the step of administering to a mammal having trypanosomiasis or leishmaniasis an amount effective to reduce the number of living protozoa in said mammal of a phenothiazine compound having a formula selected from the group consisting of:

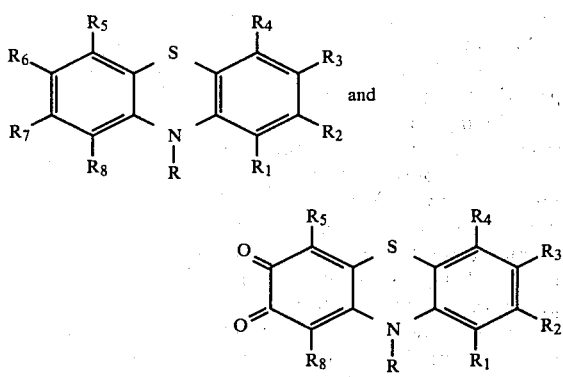

wherein R=hydrogen, $C_1$–$C_5$ alkyl, or $C_1$–$C_5$ alkyl group substituted with an amino group or with a 5- or 6-membered heterocyclic ring containing 1 or 2 nitrogen atoms selected from the group consisting of piperazinyl, piperdyl and pyrrolidinyl and $R_{1-8}$ independently represent hydrogen, halogen, hydroxyl, thiol, methylthiol, methylsulfinyl, $C_1$–$C_5$ alkyl, $C_1$–$C_6$ alkynoyl, phenyl, or trifluoromethyl.

2. The method of claim 1, wherein $R_2$, $R_3$, $R_6$, or $R_7$ is halogen, trifluoromethyl, $C_1$–$C_6$ alkynoyl, or sulfinyl.

3. The method of claim 1, wherein said compound is 2-chloro-10-[3-(dimethylamino)propyl]phenothiazine, 10-[3-(dimethylamino)propyl]phenothiazine, 2-trifluoromethyl-10-[3-(dimethylamino)propyl]phenothiazine, 2-chloro-10-[3-(4-methyl-1-piperazinyl)propyl]phenothiazine, 2-trifluoromethyl-10-[3-(4-methyl-1-piperazinyl)propyl]phenothiazine, 2-chloro-10-(3-[4-(2-hydroxyethyl)-1-piperazinyl]propyl)phenothiazine, 2-trifluoromethyl-10-(3-[4-(2-hydroxyethyl)-2-piperazinyl]propyl)phenothiazine, 2-acetyl-10-(-3-[4-(2-hydroxyethyl)-1-piperazinyl]propyl)phenothiazine, 2-butyryl-10-[3-(4-methyl-1-piperazinyl)propyl]phenothiazine, 2-propionyl-10-(3-[4-(2-hydroxyethyl)-1-piperazinyl]propyl)phenothiazine, 2-chloro-10-(3-[4-(2-hydroxyethyl)piperazinyl]propyl)phenothiazine, 2-acetyl-10-(3-[4-(2-hydroxyethyl)piperidino]propyl)phenothiazine, 2-methylthio-10-[2-(1-methyl-2-piperidyl)ethyl]phenothiazine, 2-methylsulfinyl-10-[2-(1-methyl-2-piperidyl)ethyl]phenothiazinea, 10-[2-(2-dimethylamino)propyl]phenothiazine, 10-[3-(dimethylamino)-2-methylpropyl]phenothiazine, 10-[(1-methyl-3-pyrrolidinyl)methyl]phenothiazine, 2-chlorophenothiazine, phenothiazine, 2-chloro-10-[3-(dimethylamino)propyl]phenothiazine sulfoxide, 2-chloro-7,8-dioxo-10-[3-(dimethylamino)propyl]phenothiazine, 2-chloro-7,8-dihydroxy-10-[3-(dimethylamino)propyl]phenothiazine, 2-chloro-10-(3-aminopropyl)phenothiazine, 2-chloro-7-hydroxy-10-[3-(dimethylamino)propyl]phenothiazine, or 2-chloro-8-hydroxy-10-[3-(dimethylamino)propyl]phenothiazine.

4. The method of claim 3, wherein said compound is 2-chloro-10-[3-(dimethylamino)propyl]phenothiazine, 2-chloro-7,8-dioxo-10-[3-(dimethylamino)propyl]phenothiazine, or 2-chloro-7,8-dihydroxy-10-[3-(dimethylamino)propyl]phenothiazine.

5. The method of claim 1, wherein $R_1$, $R_4$, $R_5$ and $R_8$ are hydrogen.

6. The method of claim 5, wherein R is 3(dimethylamino)propyl.

7. The method of claim 6, wherein $R_2$ is chlorine.

8. The method of claim 7, wherein $R_7$ and $R_8$ are hydrogen.

9. The method of claim 5, wherein R is 3-aminopropyl and $R_2$ is chlorine.

10. The method of claim 1, wherein R is an alkyl group having a nitrogen atom at a position 3 or 4 atoms distant from the nitrogen at position 10 of said phenothiazine compound.

11. The method of claim 10, wherein R is 3-(dimethylamino)propyl, 3-(4-methyl-1-piperazinyl)propyl, 2-(1-methyl-2-piperidyl)ethyl, or (1-methyl-3-pyrrolidinyl)methyl.

* * * * *